United States Patent [19]

Amann et al.

[11] 4,000,147
[45] Dec. 28, 1976

[54] ANHYDRO-2-MERCAPTO-1,3,4-THIADIAZOLIUM HYDROXIDES

[75] Inventors: August Amann; Horst Koenig, both of Ludwigshafen; Peter Thieme, Wachenheim; Hubert Giertz, Limburgerhof; Rolf Kretzschmar, Moorrege, all of Germany

[73] Assignee: BASF Aktiengesellschaft, Ludwigshafen (Rhine), Germany

[22] Filed: Feb. 10, 1975

[21] Appl. No.: 548,369

[30] Foreign Application Priority Data

Feb. 21, 1974 Germany .................. 2408288

[52] U.S. Cl. .................. 260/302 SD; 424/270
[51] Int. Cl.² .................. C07D 285/12
[58] Field of Search .......... 260/302 SD; 424/270

[56] References Cited
OTHER PUBLICATIONS

Potts et al., "Chemical Communications," 1968, p. 672.
Kier et al., Nature, 204, p. 697, Nov. 14, 1964.

*Primary Examiner*—Donald G. Daus
*Assistant Examiner*—D. B. Springer
*Attorney, Agent, or Firm*—Johnston, Keil, Thompson & Shurtleff

[57] ABSTRACT

New anhydro-2-mercapto-1,3,4-thiadiazolium hydroxides substituted in the 4- and 5-position, their manufacture and their use as medicaments.

7 Claims, No Drawings

ANHYDRO-2-MERCAPTO-1,3,4-THIADIAZOLIUM HYDROXIDES

The present invention relates to anhydro-2-mercapto-1,3,4-thiadiazolium hydroxides of the formula

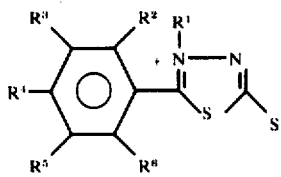

I.

in which (a) $R^2$, $R^3$, $R^4$, $R^5$ and $R^6$ are identical or different and are hydrogen, fluorine, chlorine, bromine, iodine, alkyl of 1 to 4 carbon atoms, alkoxy of 1 to 4 carbon atoms in the alkyl moiety, trifluoromethyl or $NO_2$, at least one of the substituents $R^2$ to $R^6$ being different from hydrogen, and $R^1$ is alkyl of 2 to 6 carbon atoms which is optionally substituted by OH, CN, phenyl or cycloalkyl of 3 to 6 carbon atoms in the ring, or (b) $R^1$ is methyl optionally substituted by phenyl or cycloalkyl of 3 to 6 carbon atoms in the ring when at least two of $R^2$ to $R^6$ are different from hydrogen, or, when $R^2$, $R^3$, $R^5$ and $R^6$ have the above meanings, $R^4$ is hydrogen, fluorine, bromine, iodine, alkyl of 2 to 4 carbon atoms, alkoxy of 2 to 4 carbon atoms in the alkyl moiety, trifluoromethyl or $NO_2$ and at least one of $R^2$, $R^3$, $R^4$, $R^5$ and $R^6$ is different from H, or (c) $R^2$, $R^3$, $R^4$, $R^5$ and $R^6$ are each hydrogen when $R^1$ is alkyl of 3 to 6 carbon atoms which is optionally substituted by OH, CN, phenyl or cycloalkyl of 3 to 6 carbon atoms in the ring or when $R^1$ is ethyl which is β-substituted by OH, CN, phenyl or cycloalkyl of 3 to 6 carbon atoms in the ring, or (d) $R^1$ is methyl substituted by cycloalkyl of 3 to 6 carbon atoms in the ring when $R^2$, $R^3$, $R^4$, $R^5$ and $R^6$ are each hydrogen or $R^2$, $R^3$, $R^5$ and $R^6$ are hydrogen and $R^4$ is chlorine.

The compounds have valuable pharmacological properties, in particular properties affecting the central nervous system.

The compounds of the formula I may be obtained by cyclization of a substituted thiobenzhydrazide of the formula

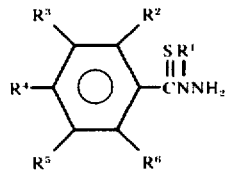

II.

in which the substituents $R^1$ and $R^6$ have the above meanings, with carbon disulfide or thiophosgene.

The cyclization reaction may be carried out in any inert solvent, at temperatures of from 0° to 100° C. Individual examples of suitable solvents are lower aliphatic alcohols, such as ethanol, acid nitriles and acid amides of lower aliphatic fatty acids, such as acetonitrile and dimethylformamide, aromatic hydrocarbons, such as benzene, and chlorinated aliphatic hydrocarbons such as methylene chloride and chloroform.

Cyclization with carbon disulfide is preferably carried out in acetonitrile at room temperature, but can also be carried out at temperatures up to the reflux point. As a rule, the resulting 1,3,4-thiadiazolium compounds of the formula I crystallize out from the reaction solution and it is only in isolated cases that the reaction solution must first be concentrated, i.e., solvent distilled off, to achieve better crystallization. The hydrogen sulfide gas formed in the reaction is conveniently trapped by means of a scrubber in series with the reactor.

In accordance with the definitions given, the substituent $R^1$ can be OH-substituted. Where such compounds are to be prepared, it is advisable to carry out cyclization with carbon disulfide rather than with thiophosgene.

When thiophosgene is used for the cyclization, the reaction is conveniently carried out in methylene chloride or chloroform as the solvent, and in the presence of an acid-binding agent, e.g., alkali metal carbonates and bicarbonates or alkaline earth metal carbonates and bicarbonates, in particular sodium carbonate, potassium carbonate, calcium carbonate and sodium bicarbonate, or tertiary organic amines, such as triethylamine and pyridine.

Analogous cyclization reactions are disclosed in the literature, e.g., K. T. Potts and C. Sapino, Chemical Communication, 1968, p. 672, or R. Grashey et al., Tetrahedron Letters, 1968, p. 5881 et seq.

The alkyl-substituted thiobenzhydrazides of the general formula II may be obtained, for example, by the method of K. A. Jensen et al., Acta Chem. Scand., 15, 1109 (1961), from the sodium salt of the corresponding 2-mercapto-S-thiobenzoylacetic acid of the formula III and a corresponding hydrazine, as shown in the equation below.

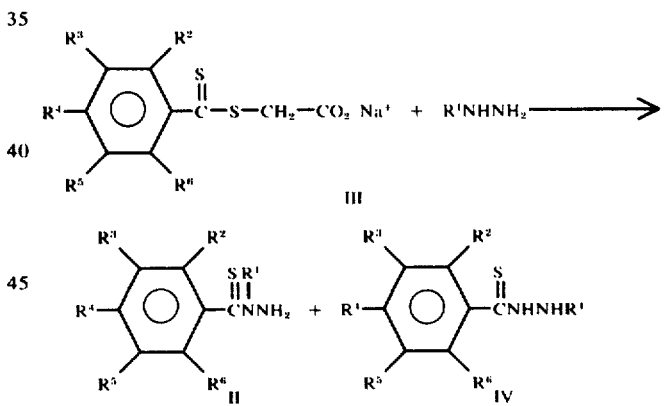

Whilst the reaction with methylhydrazine ($R^1$ = methyl) almost exclusively gives the 1-methylthiobenzhydrazides of the formula II, varying amounts of the 2-alkyl-substituted thiobenzhydrazides of the formula IV are at times also obtained in other cases.

It is desirable to separate these isomeric compounds from the 1-alkyl-substituted thiobenzhydrazides of the formula II since cyclization can give a mixture of two isomeric 1,3,4-thiadiazolium compounds which are difficult to separate. The thiobenzhydrazides can be separated by simple extraction with caustic alkali, since only the unwanted 2-alkylthiobenzhydrazide of the formula IV is able to form a salt.

The mercapto-S-(thiobenzoyl)-acetic acid of the formula III can also be obtained by the method of K. A. Jensen, loc. cit., from sodium dithiobenzoates and sodium chloroacetate. The sodium dithiobenzoates are obtained, e.g., from benzyl chlorides, sulfur and sodium methylate, by the method disclosed in German Patent 1,274,121.

The compounds according to the invention can be unsubstituted, or carry one or more substituents, in the phenyl nucleus.

Examples of monosubstituted phenyl radicals are o-, m- and p-fluorophenyl, o-, m- and p-chlorophenyl, o-, m- and p-bromophenyl, o-, m- and p-trifluoromethylphenyl, o-, m- and p-methylphenyl, methoxyphenyl, ethoxyphenyl and nitrophenyl.

Examples of disubstituted phenyl radicals are difluorophenyl, dibromophenyl, dichlorophenyl, dimethylphenyl and dimethoxyphenyl. Trimethoxyphenyl may be mentioned as a trisubstituted phenyl radical.

Specific examples of $R^1$ are methyl, ethyl, propyl, butyl, β-hydroxyethyl, β-cyanoethyl, β-hydroxypropyl, β-phenylethyl, cyclohexylmethyl and cyclopentylmethyl.

Particularly preferred compounds are those in which $R^1$ is methyl and the phenyl nucleus is substituted by fluorine or bromine in the o-, m- or p-position, by chlorine in the o- or m-position or by trifluoromethyl in the m-position.

The following compounds may be mentioned in addition to those referred to in the Examples and those listed in Table 1 (the compounds shown here and in Table 1 are obtainable in accordance with the same principles as those described in the Examples): anhydro-2-mercapto-4-β-hydroxyethyl-5-(4'-methylphenyl)-1,3,4-thiadiazolium hydroxide, anhydro-2-mercapto-4-β-cyanoethyl-5-phenyl-1,3,4-thiadiazolium hydroxide, anhydro-2-mercapto-4-methyl-5-(3'-fluorophenyl)-1,3,4-thiadiazolium hydroxide, anhydro-2-mercapto-4-ethyl-5-(4'-fluorophenyl)-1,3,4-thiadiazolium hydroxide, anhydro-2-mercapto-4-β-hydroxyethyl-5-(4'-fluorophenyl)-1,3,4-thiadiazolium hydroxide, anhydro-2-mercapto-4-(2'-hydroxypropyl)-5-(4'-fluorophenyl)-1,3,4-thiadiazolium hydroxide, anhydro-2-mercapto-4-ethyl-5-(4'-chlorophenyl)-1,3,4-thiadiazolium hydroxide, anhydro-2-mercapto-4-methyl-5-(3',5'-difluorophenyl)-1,3,4-thiadiazolium hydroxide, anhydro-2-mercapto-4-methyl-5-(2',4'-difluorophenyl)-1,3,4-thiadiazolium hydroxide, anhydro-2-mercapto-4-methyl-5-(2',6'-difluorophenyl)-1,3,4-thiadiazolium hydroxide, anhydro-2-mercapto-4-methyl-5-(2',3'-dichlorophenyl)-1,3,4-thiadiazolium hydroxide, anhydro-2-mercapto-4-methyl-5-(2',3'-difluorophenyl)-1,3,4-thiadiazolium hydroxide, anhydro-2-mercapto-4-methyl-5-(2',5'-dichlorophenyl)-1,3,4-thiadiazolium hydroxide, anhydro-2-mercapto-4-methyl-5-(2',5'-difluorophenyl)-1,3,4-thiadiazolium hydroxide and anhydro-2-mercapto-4-methyl-5-(4'-trifluoromethylphenyl)-1,3,4-thiadiazolium hydroxide.

TABLE 1

| $R^2$ | $R^3$ | $R^4$ | $R^5$ | $R^6$ | $R^1$ | Melting point °C |
|---|---|---|---|---|---|---|
| H | H | H | H | H | n-$C_3H_7$ | 109–110 |
| H | H | H | H | H | n-$C_4H_9$ | 71–73 |
| H | H | H | H | H | iso-$C_4H_9$ | 110–112 |
| H | H | H | H | H | $CH_2$—C$_6$H$_{11}$ | 150–152 |
| H | H | H | H | H | $CH_2$—$CH_2$—$C_6H_5$ | 106–108 |
| H | H | H | H | H | $CH_2$—$CH_2$—OH | 160–162 |
| H | H | H | H | H | $CH_2$—CH(CH$_3$)OH | 124–125 |
| F | H | H | H | H | $CH_3$ | 204–208 |
| H | F | H | H | H | $CH_3$ | 206–209 |
| H | H | F | H | H | $CH_3$ | 206–207 |
| Cl | H | H | H | H | $CH_3$ | 128–130 |
| H | Cl | H | H | H | $CH_3$ | 211–212 |
| H | H | Cl | H | H | n-$C_3H_7$ | 197–198 |
| H | H | Cl | H | H | n-$C_4H_9$ | 147–148 |
| H | H | Cl | H | H | iso-$C_4H_9$ | 200–202 |
| H | H | Cl | H | H | $CH_2$—$CH_2$—OH | 165 |
| H | H | Cl | H | H | $CH_2$—CH(CH$_3$)OH | 200–201 |
| H | H | Cl | H | H | $CH_2$—C$_6$H$_{11}$ | 233–234 |
| H | H | Cl | H | H | $CH_2$—cyclopentyl | 225–227 |
| H | H | Cl | H | H | $CH_2$—$CH_2$—$C_6H_5$ | 157–159 |
| H | H | Br | H | H | $CH_3$ | 208–209 |
| H | $CF_3$ | H | H | H | $CH_3$ | 179 |
| $CH_3$ | H | H | H | H | $CH_3$ | 178–180 |

TABLE 1-continued

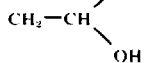

| R² | R³ | R⁴ | R⁵ | R⁶ | R¹ | Melting point °C |
|---|---|---|---|---|---|---|
| H | H | CH₃ | H | H | CH₂—CH(CH₃)(OH) | 188-191 |
| H | H | C₂H₅O | H | H | CH₃ | 193-194 |
| H | H | NO₂ | H | H | CH₃ | 234-236 |
| H | Cl | Cl | H | H | CH₃ | 209-212 |
| CH₃ | H | CH₃ | H | H | CH₃ | 146-148 |
| CH₃ | H | H | CH₃ | H | CH₃ | 158-159 |
| H | CH₃O | CH₃O | CH₃O | H | CH₃ | 208-209 |
| H | Cl | H | Cl | H | CH₃ | 223 |
| Cl | H | Cl | H | H | CH₃ | 222-224 |
| Cl | H | H | H | Cl | CH₃ | 230-232 |

The compounds according to the invention are distinguished by a pronounced anti-convulsive action coupled with very low toxicity (Table 2). This action is particularly advantageous because other neuro-pharmacological effects, for example a sedative action or prolongation of the duration of hexobarbital narcosis, only manifest themselves at relatively high doses, so that a very advantageous therapeutic breadth is provided for animal experiments.

The compounds can be used for the therapy and prophylaxis of psychomotor cramps and epilepsy (grand mal and petit mal) or in electric shock therapy.

As a pharmacological test of the anti-convulsive action against clonic spasms caused by Pentetrazol, the test substances were administered orally to groups of from 8 to 10 female Swiss mice weighing from 20 to 25 g, 30 minutes before subcutaneous administration of 60 mg/kg of Pentetrazol.

In the untreated animals, this dose of Pentetrazol caused clonic cramps, as a result of which the mice slid off an inclined screen.

Anti-convulsive agents prevent the cramps and the sliding off the screen, the degree of prevention depending on the dose. The ED₅₀ was taken to be the dose after administration of which 50% of the treated animals remained on the screen.

TABLE 2

| R¹ | X | Anti-convulsive action, ED₅₀ (mg/kg)[1] | Acute toxicity, LD₅₀ (mg/kg)[2] |
|---|---|---|---|
| CH₃ | 2-F-phenyl | 10.0 | >1000 |
| CH₃ | 3-F-phenyl | 2.2 | 1000 |
| CH₃ | 4-F-phenyl | 2.2 | >1000 |

TABLE 2-continued

| R¹ | X | Anti-convulsive action, ED₅₀ (mg/kg)[1] | Acute toxicity, LD₅₀ (mg/kg)[2] |
|---|---|---|---|
| CH₃ | 3-Cl-phenyl | 3.2 | >1000 |
| CH₃ | 3-Br-phenyl | 46.0 | >1000 |
| C₃H₇ | 3-Cl-phenyl | 32.0 | 681· |
| C₃H₇ | phenyl | 22.0 | 68.1 |
| CH₃ | 3-CF₃-phenyl | 0.46 | 681 |

[1]Action against clonic cramps caused by Pentetrazol in mice. Oral administration 30 minutes before subcutaneous administration of 60 mg/kg of Pentetrazol
[2]Mice. Intraperitoneal administration. Approximate values The anti-convulsive effectiveness of the compounds according to the invention is markedly superior to that of conventional anti-convulsive agents. Comparative experiments with Phenytoin, Phenobarbital and Trimethadion were carried out on mice, in relation to the maximum tonic extension spasm after subcutaneous administration of 121 mg/kg of Pentetrazol, the minimum clonic cramp after subcutaneous administration of 70 mg/kg of Pentetrazol and the maximum tonic electro-induced cramp (Table 3).

The comparative experiments in Table 3 were carried out with anhydro-2-mercapto-4-methyl-5-(3'-chlorophenyl)-1,3,4-thiadiazolium hydroxide, referred to as substance A in the Table and in the subsequent text.

TABLE 3

| Substance | Maximum Pentetrazol-induced extension | Minimum Pentetrazol-induced cramp | Maximum electric shock | Toxicity |
|---|---|---|---|---|
| | ED$_{50}$ (mg/kg administered orally) | | | LD$_{50}$ |
| Substance A | 10 | 7 | 23 | >1,000 |
| Phenytoin | 22 | inactive | 8 | 360 |
| Phenobarbital | 22 | 30 | 11 | 320 |
| Trimethadion | 260 | 240 | 450 | >1,000 |

In the Table, the ED$_{50}$ values indicate protection against clonic cramps induced by Pentetrazol, as observed 45 minutes after administration of the latter, and protection against tonic cramps induced by electric shock.

The toxicity of substance A is markedly less than that of Phenobarbital and Phenytoin. On the other hand, the compound is more active in counteracting clonic spasms induced by Pentetrazol than is Phenobarbital and above all than is Phenytoin, which in the present test is inactive. In tonic cramp experimentally induced by Pentetrazol, and in cramp induced by electric shock, Phenobarbital and Phenytoin are only about twice as active (as substance A). Trimethadion is more than 20 times less active than substance A, both in the clonic cramp test and in the tonic cramp test.

A pharmaceutical preparation, in the form of a dosage unit suitable for administration, can be prepared by conventional methods with the aid of a suitable inert carrier or diluent and the conventional pharmaceutical auxiliaries. The amount of active compound is such that one or more units are normally required for a single therapeutic administration.

Suitable pharmaceutical preparations for the treatment of various forms of epilepsy and various degrees of severity thereof contain, as a rule, about from 1 to 300 mg of one of the compounds of the invention as a single dose for adult or juvenile humans.

A preferred pharmaceutical preparation is a form suitable for oral administration, including, e.g., tablets, dragees, capsules and elixirs, which can be prepared by conventional methods by those skilled in the art.

As a rule the preparations consist of the active ingredient mixed with a carrier, or diluted with a carrier, or filled into or encapsulated by a carrier in the form of a capsule or other container as a carrier substance which may serve as a medium, flavoring agent or diluent for the therapeutically active ingredient. This carrier may be a solid, semi-solid or liquid substance.

Examples of carriers which may be used are: lactose, dextrose, sucrose, sorbitol, mannitol, starch, gum acacia, coconut butter, cocoa butter, alginates, tragacanth, gelatins, invert sugar syrup, methylcellulose, polyoxyethylenesorbitan monolaurate, methyl hydroxybenzoate and propyl hydroxybenzoate. When preparing tablets a lubricant may be added to prevent the powdered components from sticking in the tablet mold or tablet press. Examples of suitable lubricants are talc, aluminum stearate, magnesium stearate and calcium stearate.

EXAMPLE 1

2-mercapto-S-thiobenzoylacetic acid

At room temperature, 126.6 g (1.0 mole) of benzyl chloride is added dropwise in the course of one hour to a mixture of 64 g (2 moles) of ground sulfur in 500 ml of absolute methanol and 396 g of 30% strength sodium methylate solution. The mixture turns red and the temperature rises to the boil. The mixture is then refluxed for 16 hours. Thereafter it is cooled, the sodium chloride formed is filtered off and washed with methanol and the mother liquor is concentrated by evaporation. 252 g of sodium dithiobenzoate is obtained as a red oil which is taken up in 600 ml of water; the solution is cooled to 0° C and 116.5 g (1.5 moles) of the sodium salt of chloroacetic acid is added, during which addition the temperature should not rise above +5° C. The mixture is stirred for a further 2 hours and the reaction vessel is then kept at 0° C for 48 hours. The solution is then washed twice, each time with 100 ml of methylene chloride, and subsequently acidified with concentrated aqueous hydrochloric acid. A deep red precipitate separates out, and is filtered off, dried and recrystallized from methylene chloride/petroleum ether. Yield 195 g (92% of theory), melting point 117° to 119° C.

The following substituted 2-mercapto-S-thiobenzoylacetic acids of the formula III were prepared analogously to Example 1: 2-mercapto-S-(2'-fluorothiobenzoyl)-acetic acid, melting point 81° to 83° C, yield 63%; 2-mercapto-S-(3'-fluorothiobenzoyl)-acetic acid, melting point 112° to 114° C, yield 72%; 2-mercapto-S-(4'-fluorothiobenzoyl)-acetic acid, melting point 120° to 122° C, yield 68%; 2-mercapto-S-(2'-chlorothiobenzoyl)-acetic acid, oil, yield 71%; 2-mercapto-S-(3'-chlorothiobenzoyl)-acetic acid, melting point 123° to 125° C, yield 58%; 2-mercapto-S-(4'-chlorothiobenzoyl)-acetic acid, melting point 112° to 114° C, yield 69%; 2-mercapto-S-(4'-bromothiobenzoyl)-acetic acid, melting point 105° to 107° C, yield 46%; 2-mercapto-S-(3'-trifluoromethylthiobenzoyl)-acetic acid, melting point 78° to 82° C, yield 48%; 2-mercapto-S-(2'-methylthiobenzoyl)-acetic acid, melting point 121° to 122° C, yield 56%; 2-mercapto-S-(4'-methylthiobenzoyl)-acetic acid, melting point 118° to 119° C, yield 57%; 2-mercapto-S-(4'-ethoxythiobenzoyl)-acetic acid, not isolated, used directly for further conversions; 2-mercapto-S-(4'-nitrothiobenzoyl)-acetic acid, not isolated, used directly for further conversions; 2-mercapto-S-(3',4'-dichlorothiobenzoyl)-acetic acid, not isolated, used directly for further conversions; 2-mercapto-S-(2',4'-dimethylthiobenzoyl)-acetic acid, melting point 150° to 152° C, yield 63%; 2-mercapto-S-(2',5'-dimethylthiobenzoyl)-acetic acid, melting point 107° to 109° C, yield 55%; 2-mercapto-S-(3',4',5'-trimethoxythiobenzoyl)-acetic acid, melting point 124° to 126° C, yield 51%; 2-mercapto-S-(3',5'-dichlorothiobenzoyl)-acetic acid, melting point 109° to 111° C, yield 58%; 2-mercapto-S-(2',4'-dichlorothiobenzoyl)-acetic acid, melting point 128° to 130° C, yield 72% and 2-mercapto-S-(2',6'-dichlorothiobenzoyl)-acetic acid, melting point 120° to 122° C, yield 35%.

EXAMPLE 2

Preparation of 1-methyl-1-(4'-fluorothiobenz)-hydrazide 40.9 g (178 millimoles) of 2-mercapto-S-(4'-fluorothiobenzoyl)-acetic acid is dissolved in 178 ml of normal sodium hydroxide solution, and 8.4 g (178 millimoles) of methylhydrazine in 10 ml of water is added dropwise at 0° C. The mixture is stirred for a further hour at 0° C and the precipitate is filtered off, washed with water and recrystallized from ethanol. 25.8 g (79% of theory) of pale yellow crystals of melting point 80° to 82° C are obtained.

The following 1-methylthiobenzhydrazides corresponding to the formula II were prepared analogously: 1-methyl-1-(2'-fluorothiobenz)-hydrazide, melting point 88° to 90° C, yield 79%; 1-methyl-1-(3'-fluorothiobenz)-hydrazide, melting point 48° C, yield 72%; 1-methyl-1-(2'-chlorothiobenz)-hydrazide, melting point 122° to 124° C, yield 66%; 1-methyl-1-(3'-chlorothiobenz)-hydrazide, melting point 87° to 89° C, yield 82%; 1-methyl-1-(4'-bromothiobenz)-hydrazide, melting point 123° to 125° C, yield 43%; 1-methyl-1-(3'-trifluoromethylthiobenz)-hydrazide, melting point 38° to 41° C, yield 68%; 1-methyl-1-(4'-ethoxythiobenz)-hydrazide, melting point 75° to 76° C, yield 72%; 1-methyl-1-(2'-methylthiobenz)-hydrazide, melting point 70° to 72° C, yield 26%; 1-methyl-1-(4'-nitrothiobenz)-hydrazide, melting point 146° to 150° C, yield 12%; 1-methyl-1-(3',4'-dichlorothiobenz)-hydrazide, melting point 99° to 100° C, yield 36%; 1-methyl-1-(2',4'-dimethylthiobenz)-hydrazide, melting point 100° to 101° C, yield 24%; 1-methyl-1-(2',5'-dimethylthiobenz)-hydrazide, melting point 70° to 72° C, yield 61%; 1-methyl-1-(3',4'-dioxymethylenethiobenz)-hydrazide, melting point 76° to 78° C, yield 56%; 1-methyl-1-(3',4',5'-trimethoxythiobenz)-hydrazide, melting point 98° to 100° C, yield 69%; 1-methyl-1-(3',5'-dichlorothiobenz)-hydride, melting point 110° to 112° C, yield 83% and 1-methyl-1-(2',4'-dichlorothiobenz)-hydrazide, melting point 93° to 95° C, yield 39%.

EXAMPLE 3

1-isobutyl-1-(4'-chlorothiobenz)-hydrazide 36.9 g (0.15 mole) of 2-mercapto-5-(4'-chlorothiobenzoyl)-acetic acid was suspended in 200 ml of water, and 150 ml of normal sodium hydroxide solution was added at below 5° C. 15.2 g (0.17 mole) of isobutylhydrazine in 20 ml of water was then added dropwise to the solution at below 5° C. The mixture is stirred for 3 hours at room temperature, acidified with acetic acid and extracted repeatedly with methylene chloride. The combined methylene chloride phases are extracted three times, each time with 60 ml of normal sodium hydroxide solution. The methylene chloride phase which remains is dried over sodium sulfate and concentrated by evaporation. 7.8 g (22% of theory) of an oil is obtained; the spectra indicate that the structure agrees with that of the desired 1-isobutyl-1-(4'-chlorothiobenz)-hydrazide. 25.8 g (71% of theory) of the unwanted 2-isobutyl-1-(4'-chlorothiobenz)-hydrazide can be obtained from the alkaline extracts by acidification with acetic acid.

The 1-alkyl-1-thiobenzhydrazides shown below were obtained analogously to Example 3. They were in the main obtained as oils which were cyclized, without further purification, to 1,3,4-thiadiazole derivatives: 1-n-propyl-1-thiobenzhydrazide, 1-n-butyl-1-thiobenzhydrazide, 1-isobutyl-1-thiobenzhydrazide, 1-cyclopentylmethyl-1-thiobenzhydrazide, 1-cyclohexylmethyl-1-thiobenzhydrazide, 1-(2-phenylethyl)-1-thiobenzhydrazide, 1-(2-hydroxyethyl)-1-thiobenzhydrazide, 1-(2-hydroxypropyl)-1-thiobenzhydrazide, 1-(2-cyanoethyl)-1-thiobenzhydrazide, 1-ethyl-1-(4'-fluorothiobenz)-hydrazide, 1-(2-hydroxyethyl)-1-(4'-fluorothiobenz)-hydrazide, 1-(2-hydroxypropyl)-1-(4'-fluorothiobenz)-hydrazide, 1-(2-hydroxypropyl)-1-(4'-fluorothiobenz)-hydrazide, 1-ethyl-1-(4'-chlorothiobenz)-hydrazide, 1-n-propyl-1-(4'-chlorothiobenz)-hydrazide, 1-n-butyl-1-(4'-chlorothiobenz)-hydrazide, 1-(2-hydroxyethyl)-1-(4'-chlorothiobenz)-hydrazide, 1-(2-hydroxypropyl)-1-(4'-chlorothiobenz)-hydrazide, 1-cyclopentylmethyl-1-(4'-chlorothiobenz)-hydrazide, 1-cyclohexylmethyl-1-(4'-chlorothiobenz)-hydrazide, 1-(2-phenylethyl)-1-(4'-chlorothiobenz)-hydrazide, 1-(2-hydroxyethyl)-1-(4'-methylthiobenz)-hydrazide and 1-(2-hydroxypropyl)-1-(4'-methylthiobenz)-hydrazide.

EXAMPLE 4

Anhydro-2-mercapto-4-methyl-5-(4'-fluorophenyl)-1,3,4-thiadiazolium hydroxide 8 g (41 millimoles) of 1-methyl-1-(4'-fluorothiobenz)-hydrazide in 50 ml of absolute acetonitrile are refluxed with carbon disulfide for 3 hours. After cooling, 7.5 g of yellow crystals melting at from 206° to 207° C are obtained. Yield: 80% of theory.

$C_9H_7FN_2S_2$; (226.3); Calculated: C, 47.77; H, 3.12; N, 12.39; F, 8.40. Found: C, 47.7; H, 3.8; N, 12.6; F, 8.4.

EXAMPLE 5

Anhydro-2-mercapto-4-(2-hydroxyethyl)-5-phenyl-1,3,4-thiadiazolium hydroxide 9.8 g (0.05 mole) of 1-(2-hydroxyethyl)-1-thiobenzhydrazide is dissolved in 30 ml of absolute acetonitrile, and 4 ml of carbon disulfide is added. The mixture is refluxed for 3 hours and after cooling, 5.2 g (44% of theory) of yellow crystals melting at from 160° to 162° C are obtained.

$C_{10}H_{10}N_2S_2O$ (238.3) Calculated: C, 50.40; H, 4.23; N, 11.75; Found: 50.6; 4.3; 11.9.

The anhydro-2-mercapto-1,3,4-thiadiazolium hydroxides listed below are prepared analogously to Examples 4 and 5. They are obtained, in the main, as pale to deep golden yellow crystalline products which can be recrystallized from alcohol or dimethylformamide or mixtures of these solvents: anhydro-2-mercapto-4-n-propyl-5-phenyl-1,3,4-thiadiazolium hydroxide, melting point 109° to 110° C; anhydro-2-mercapto-4-n-butyl-5-phenyl-1,3,4-thiadiazolium hydroxide, melting point 71° to 73° C; anhydro-2-mercapto-4-isobutyl-5-phenyl-1,3,4-thiadiazolium hydroxide, melting point 110° to 112° C; anhydro-2-mercapto-4-cyclopentylmethyl-5-phenyl-1,3,4-thiadiazolium hydroxide, melting point 114° to 115° C; anhydro-2-mercapto-4-cyclohexylmethyl-5-phenyl-1,3,4-thiadiazolium hydroxide, melting point 150° to 152° C; anhydro-2-mercapto-4-(2-phenylethyl)-5-phenyl-1,3,4-thiadiazolium hydroxide, melting point 106° to 108° C; anhydro-2-mercapto-4-(2-hydroxypropyl)-5-phenyl-1,3,4-thiadiazolium hydroxide, melting point 124° to 125° C; anhydro-2-mercapto-4-methyl-5-(2'-fluorophenyl)-1,3,4-thiadiazolium hydroxide, melting point 204° to 208° C; anhydro-2-mercapto-4-methyl-5-(3'-fluorophenyl)-1,3,4-thiadiazolium hydroxide, melting point 206° to 209° C; anhydro-2-mercapto-4-methyl-5-(2'-chlorophenyl)-1,3,4-thiadiazolium hydroxide, melting point 128° to 130° C; anhydro-2-mercapto-4-methyl-4-(3'-chlorophenyl)-1,3,4-thiadiazolium hydroxide, melting point 211° to 212° C; anhydro-2-mercapto-4-n-propyl-5-(4'-chlorophenyl)-1,3,4-thiadiazolium hydroxide, melting point 197° to 198° C; anhydro-2-mercapto-4-n-butyl-5-(4'-chlorophenyl)-1,3,4- thiadiazolium hydroxide, melting point 147° to 148° C; anhydro-2-mercapto-4-isobutyl-5-(4'-chlorophenyl)-1,3,4-thiadiazolium hydroxide, melting point 200° to 202° C; anhydro-2-mercapto-4-cyclopentylmethyl-4-(4'-chlorophenyl)-1,3,4-thiadiazolium hydroxide, melting point 225° to 227° C; anhydro-2-mercapto-4-cyclohexylmethyl-5-(4'-chlorophenyl)-1,3,4-thiadiazolium hydroxide, melting point 233° to 234° C; anhydro-2-mercapto-4-(2-phenylethyl)-5-(4'-chlorophenyl)-1,3,4-thiadiazolium hydroxide, melting point 157° to 159° C; anhydro-2-mercapto-4-(2-hydroxyethyl)-5-(4'-chlorophenyl)-1,3,4-thiadiazolium hydroxide, melting point 165° C; anhydro-2-mercapto-4-(2-hydroxypropyl)-5-(4'-chlorophenyl)-1,3,4-thiadiazolium hydroxide, melting point 200° to 201° C; anhydro-2-mercapto-4-methyl-5-(4'-bromophenyl)-1,3,4-thiadiazolium hydroxide, melting point 208° to 209° C; anhydro-2-mercapto-4-methyl-5-(3'-trifluoromethylphenyl)-1,3,4,-thiadiazolium hydroxide, melting point 179° C; anhydro-2-mercapto-4-methyl-5-(2'-methylphenyl)-1,3,4-thiadiazolium hydroxide, melting point 178° to 180° C; anhydro-2-mercapto-4-(2-hydroxypropyl)-5-(4'-methylphenyl)-1,3,4-thiadiazolium hydroxide, melting point 188° to 191° C; anhydro-2-mercapto-4-methyl-5-(4'-ethoxyphenyl)-1,3,4-thiadiazolium hydroxide, melting point 193° to 194° C; anhydro-2-mercapto-4-methyl-5-(4'-nitrophenyl)-1,3,4-thiadiazolium hydroxide, melting point 234° to 236° C; anhydro-2-mercapto-4-methyl-5-(3',4'-dichlorophenyl)-1,3,4-thiadiazolium hydroxide, melting point 209° to 212° C; anhydro-2-mercapto-4-methyl-5-(2',4'-dimethylphenyl)-2,3,4-thiadiazolium hydroxide, melting point 146° to 148° C; anhydro-2-mercapto-4-methyl-5-(2',5'-dimethylphenyl)-1,3,4-thiadiazolium hydroxide, melting point 158° to 159° C; anhydro-2-mercapto-4-methyl-5-(3',4',5'-trimethoxyphenyl)-1,3,4-thiadiazolium hydroxide, melting point 208° to 209° C; anhydro-2-mercapto-4-methyl-5-(2',4'-dichlorophenyl)-1,3,4-thiadiazolium hydroxide, melting point 222° to 224° C and anhydro-2-mercapto-4-methyl-5-(3',5'-dichlorophenyl)-1,3,4-thiadiazolium hydroxide, melting point 223° C.

EXAMPLES OF PHARMACEUTICAL PREPARATIONS

EXAMPLE 1 (Tablets)

| | |
|---|---|
| Active ingredient - substance A | 10.0 mg |
| Lactose | 89.0 mg |
| Magnesium stearate | ad 100.0 mg |

The active ingredient is mixed with the lactose, the mixture is granulated by conventional methods, magnesium stearate is added and tablets having a final weight of 100 mg are pressed from the mixture by conventional methods.

EXAMPLE 2 (Dragées)

| | |
|---|---|
| Active ingredient - substance A | 100.0 mg |
| Lactose | 30.0 mg |
| Avicel talc | 25.0 mg |
| Talc | ad 160.0 mg |

The constituents are mixed and tablets of 8 mm diameter and weighing 160 mg are pressed from the mixture by conventional methods; these tablets are then coated with sugar syrup to give a final weight of 250 mg.

EXAMPLE 3 (Capsules)

| | |
|---|---|
| Active ingredient - substance A | 300.0 mg |
| Talc | 10.0 mg |

The active ingredient is mixed with the talc and the mixture is filled into gelatin capsules.

EXAMPLE 4 (Elixir)

| | |
|---|---|
| Active ingredient - substance A | 1.0 g |
| Bentonite | 2.0 g |
| Sodium carboxymethylcellulose | 1.5 g |
| Sugar | 30.0 g |
| Potassium sorbate | 0.3 g |
| Peppermint flavoring | 0.01 g |
| Water | ad 100.0 g |

A suspension elixir is prepared by conventional methods from the finely ground active ingredient and the stated auxiliaries. The individual dose is one teaspoonful.

We claim:
1. 1-Anhydro-2-mercapto-1,3,4-thiadiazolium hydroxides of the formula

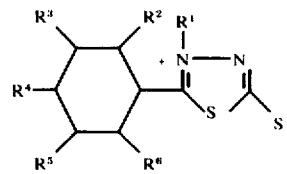

in which $R^1$ is methyl, $R^2$, $R^3$, $R^5$ and $R^6$ are hydrogen, fluorine, chlorine, bromine or iodine, $R^4$ is hydrogen, fluorine, bromine or iodine and at least one and no more than two of $R^2$, $R^3$, $R^4$, $R^5$ and $R^6$ is different from H.

2. 1-Anhydro-2-mercapto-1,3,4-thiadiazolium hydroxides as set forth in claim 1 in which the phenyl nucleus is substituted by fluorine or bromine in the o-, m- or p-position or by chlorine in the o- or m-position.

3. Anhydro-2-mercapto-4-methyl-5-(3'-chlorophenyl)-1,3,4-thiadiazolium hydroxide.

4. Anhydro-2-mercapto-4-methyl-5-(2'-fluorophenyl)-1,3,4-thiadiazolium hydroxide.

5. Anhydro-2-mercapto-4-methyl-5-(3'-fluorophenyl)-1,3,4-thiadiazolium hydroxide.

6. Anhydro-2-mercapto-4-methyl-5-(4'-fluorophenyl)-1,3,4-thiadiazolium hydroxide.

7. Anhydro-2-mercapto-4-methyl-5-(4'-bromophenyl)-1,3,4-thiadiazolium hydroxide.

* * * * *